United States Patent
Gallina et al.

(10) Patent No.: US 11,332,467 B2
(45) Date of Patent: May 17, 2022

(54) SOLID STATE FORMS OF PALBOCICLIB DIMESYLATE

(71) Applicant: PLANTEX LTD., Petach-Tikva (IL)

(72) Inventors: Maurizio Gallina, Novara (IT); Paolo Angioletti, Lainate (IT); Paolo S. Tiseni, Bresso (IT); Marina Ratkaj, Zagreb (HR)

(73) Assignee: PLANTEX LTD., Petach-Tikva (IL)

( * ) Notice: Subject to any disclaimer, the term of this patent is extended or adjusted under 35 U.S.C. 154(b) by 3 days.

(21) Appl. No.: 16/810,914

(22) Filed: Mar. 6, 2020

(65) Prior Publication Data

US 2020/0199125 A1 Jun. 25, 2020

Related U.S. Application Data

(63) Continuation of application No. 16/315,816, filed as application No. PCT/US2017/041005 on Jul. 7, 2017, now Pat. No. 10,597,393.

(60) Provisional application No. 62/359,423, filed on Jul. 7, 2016.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01); *C07B 2200/13* (2013.01)

(58) Field of Classification Search
CPC .............................. C07D 471/04; A61P 35/00
See application file for complete search history.

(56) References Cited

U.S. PATENT DOCUMENTS

| | | | |
|---|---|---|---|
| 10,597,393 | B2 | 3/2020 | Gallina et al. |
| 2018/0319790 | A1 | 11/2018 | Fan et al. |

FOREIGN PATENT DOCUMENTS

| | | |
|---|---|---|
| CN | 104478874 A | 4/2015 |
| CN | 105085517 A | 11/2015 |
| CN | 105111205 A | 12/2015 |
| CN | 105418603 A | 3/2016 |
| JP | 2014162794 A | 9/2014 |
| WO | 03062236 A1 | 7/2003 |
| WO | 2005005426 A1 | 1/2005 |
| WO | 2008032157 A2 | 3/2008 |
| WO | 2014128588 A1 | 8/2014 |
| WO | 2016066420 A1 | 5/2016 |
| WO | 2016090257 A1 | 6/2016 |
| WO | 2016092442 A1 | 6/2016 |
| WO | 2016156070 A1 | 10/2016 |
| WO | 2017145054 A1 | 8/2017 |
| WO | 2018007927 A1 | 1/2018 |
| WO | 2018065999 A1 | 4/2018 |
| WO | 2018073574 A1 | 4/2018 |

OTHER PUBLICATIONS

Shengquan Duan, et al., "Palbociclib Commercial Manufacturing Process Development. Part I: Control of Regioselectivity in a Grignard-Mediated SNAr Coupling", Organic Process Research & Development vol. 20, No. 7, pp. 1191-1202 (2016).
Mark T. Maloney, et al., "Palbociclib Commercial Manufacturing Process Development. Part II: Regioselective Heck Coupling with Polymorph Control for Processability", Organic Process Research &Development (2016).
Brian P. Chekal, et al., "Palbociclib Commercial Manufacturing Process Development. Part III. Deprotection Followed by Crystallization for API Particle Property Control", Organic Process Research & Development, vol. 20, No. 7, pp. 1217-1226 (2016).
Authors et al: disclosed anonymously, "Process for the Preparation of Palbociclib Crystalline Forms", IP.com prior art database technical disclosure, IP.com No. IPCOM000246804D (2016).
Japanese Office Action issued in corresponding Appl. No. JP 2019-520931, dated Dec. 2, 2019, together with English language translation (13 pages).
AJ. Cruz-Cabeza et al., 44 Chemical Society Reviews, 8619-8635 (2015) (Year: 2015).
Solid State Characterization of Pharmaceuticals 473-491, 490 (R.A. Storey et al., eds., 2011) (Year: 2011).
Dialog English Language Machine Translation of CN 105085517 (2015) (Year: 2015).
CAS Abstract of CN 105085517 (2015) (Year: 2015).
ESpace English Language Machine Translation of CN 105085517 (2015) (Year: 2015).
Caira, Mino R.; "Crystalline Polymorphism of Organic Compounds"; Topics in Current Chemistry, vol. 198: 1998, p. 163-208.
International Search Report for International Application No. PCT/US2017/041005, International Filing Date Jul. 7, 2017, dated Oct. 12, 2017, 4 pages.
Written Opinion for International Application No. PCT/US2017/041005, International Filing Date Jul. 7, 2017, dated Oct. 12, 2017, 6 pages.
Office Action issued in corresponding Mexican application MX/a/2019/000246 dated Mar. 11, 2021 (8 pages) including English language translaiton (6 pages).
Office Action issued in corresponding Mexican Application No. MX/a/2019/000246 dated Sep. 11, 2020 (9 pages) together with English language translation (6 pages).
Office Action issued in corresponding Mexican application MX/a/2019/000246, dated Oct. 7, 2021, including English language translation (31 pages).
Notice of Opposition issued in corresponding JP Patent No. 6870082 dated Nov. 12, 2021 (43 pages).
Office Action (Notice of Reason for Revocation) issued in corresponding JP Patent No. 6870082 dated Feb. 4, 2022 (17 pages).

*Primary Examiner* — Susanna Moore
(74) *Attorney, Agent, or Firm* — Carter, DeLuca & Farrell LLP

(57) ABSTRACT

Solid state forms of Palbociclib dimesylate, processes for preparation thereof and use thereof for preparation of Palbociclib are disclosed.

13 Claims, 12 Drawing Sheets

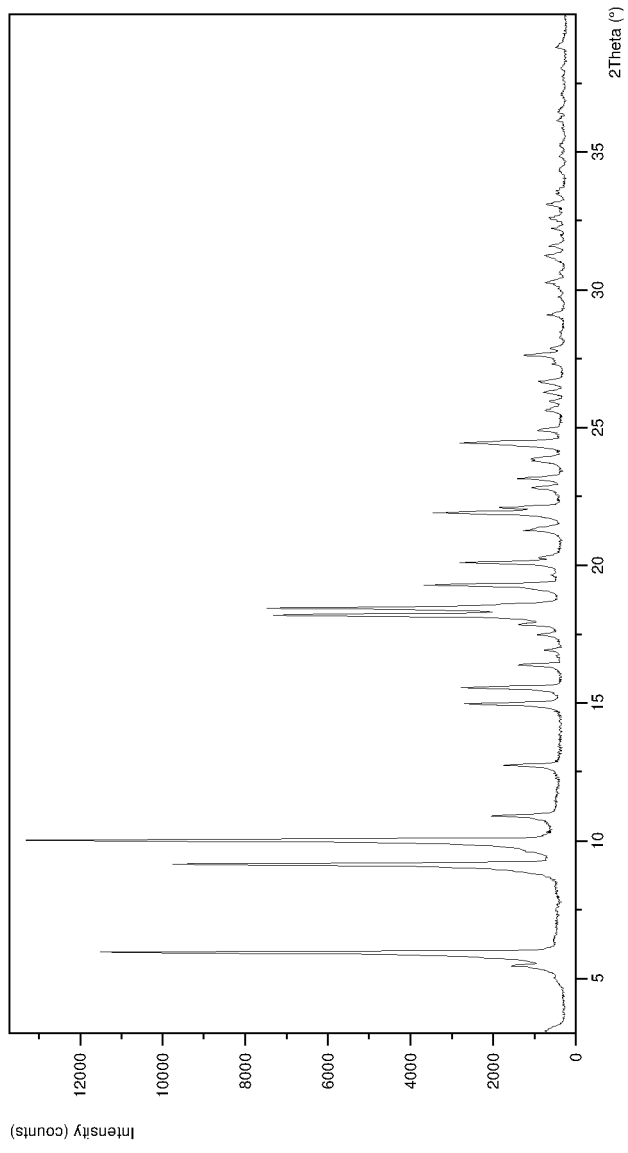
Figure 1. X-ray powder diffractogram of Form E of Palbociclib dimesylate.

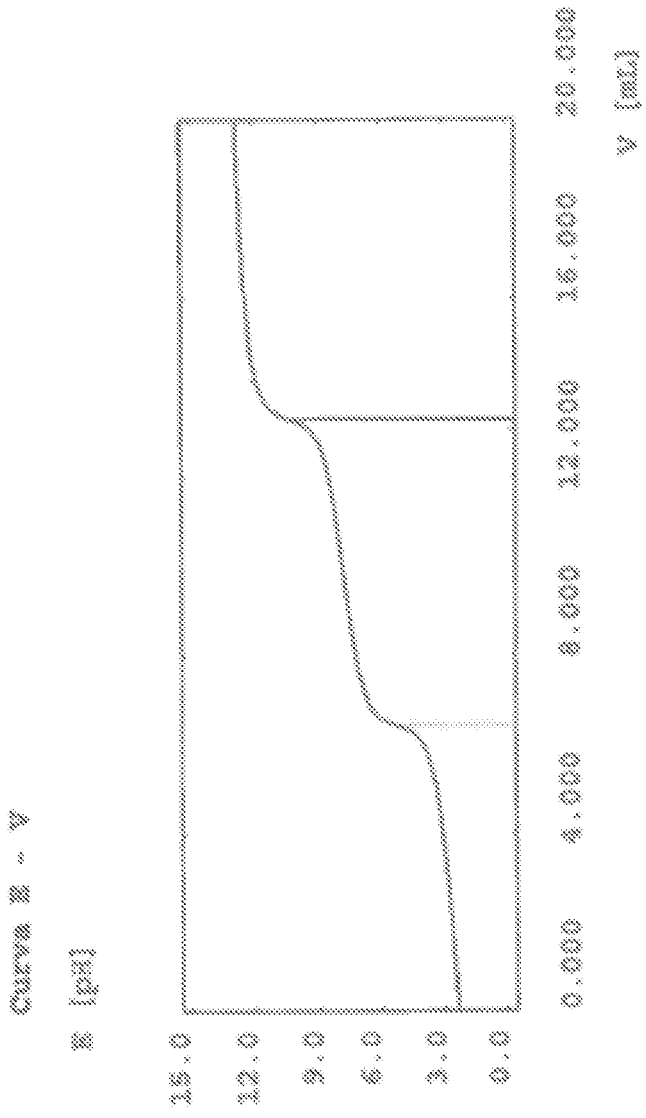
Figure 2. Potentiometric titration of form E of Palbociclib dimesylate

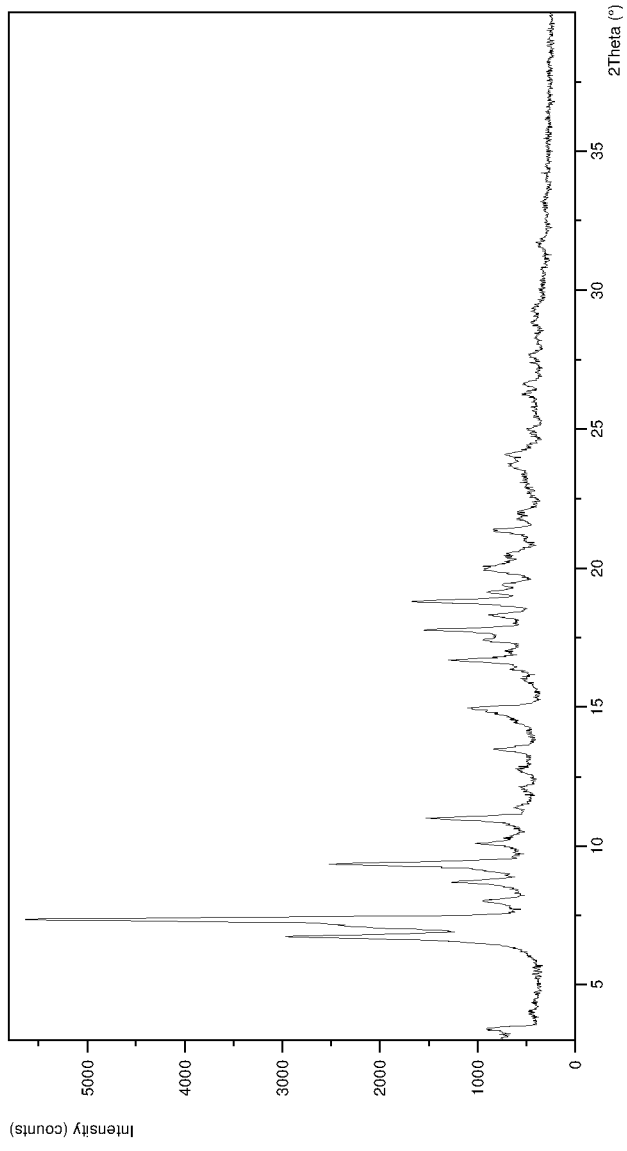
Figure 3. X-ray powder diffractogram of Form F of Palbociclib dimesylate.

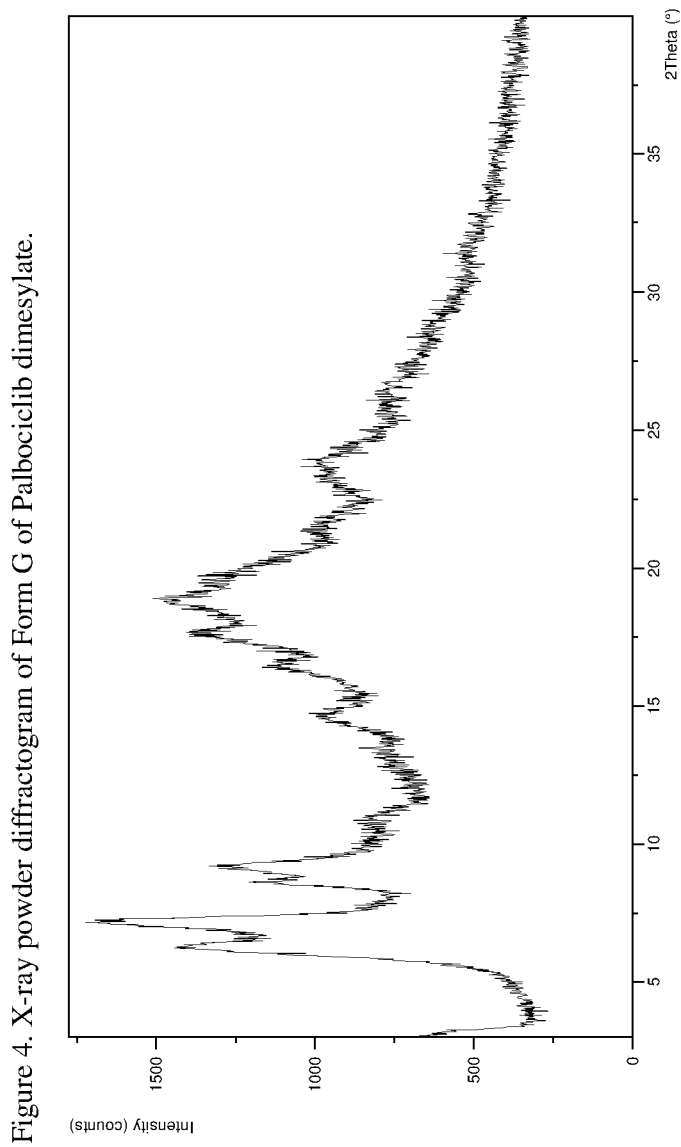
Figure 4. X-ray powder diffractogram of Form G of Palbociclib dimesylate.

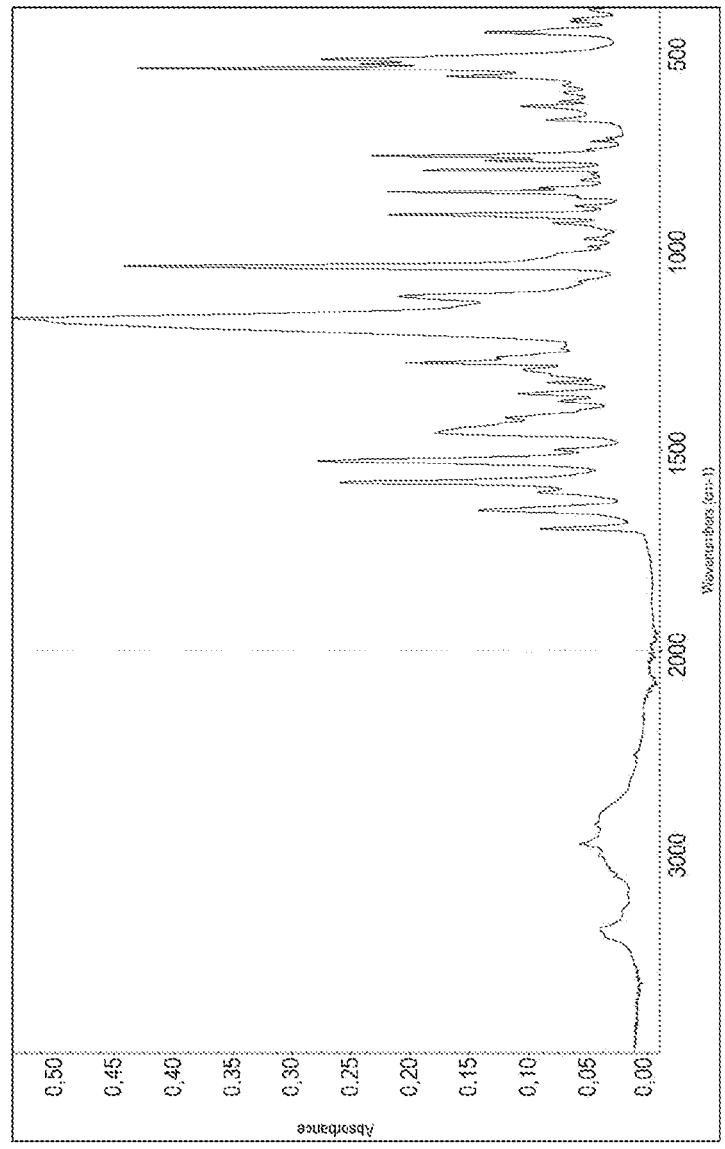
Figure 5. FTIR spectrum of Form E of Palbociclib dimesylate.

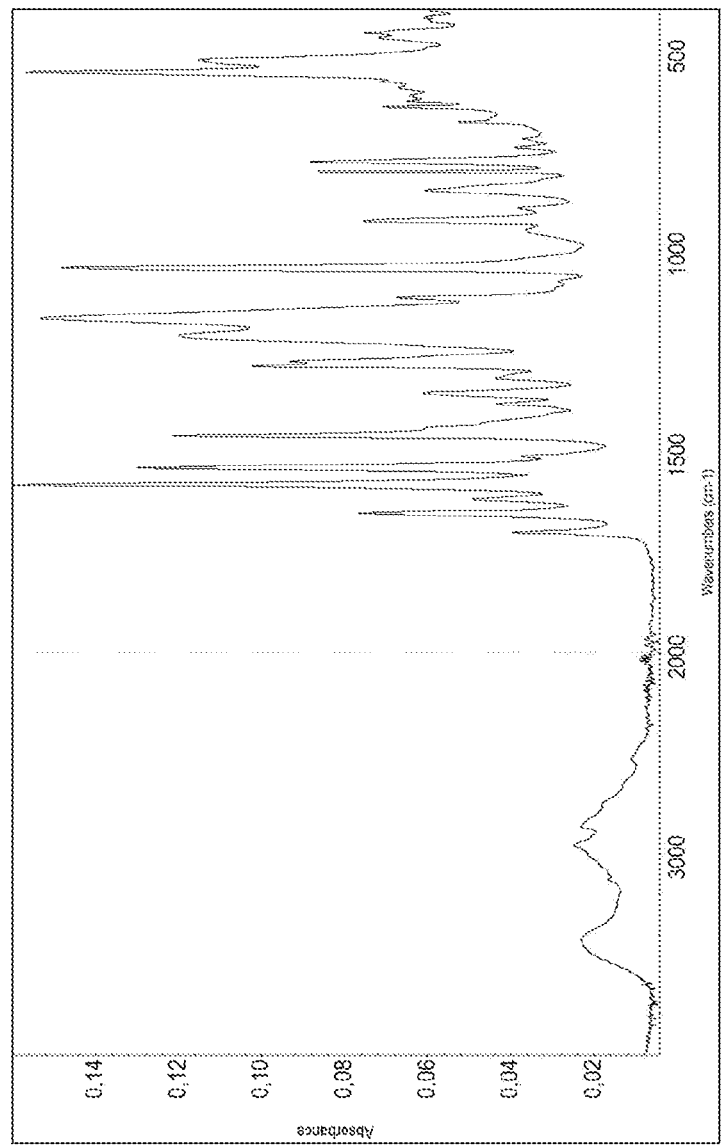
Figure 6. FTIR spectrum of Form F of Palbociclib dimesylate.

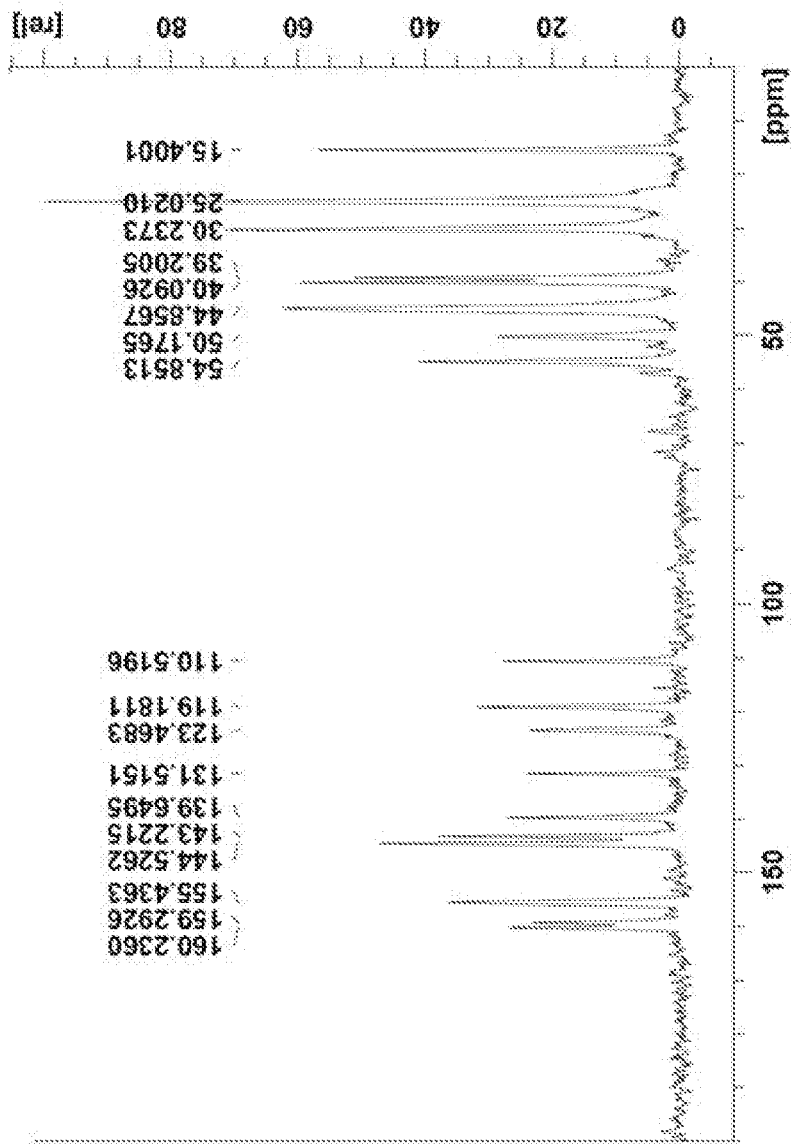
Figure 7. Solid State $^{13}$C NMR spectrum of Form E of Palbociclib dimesylate (Full range- 200-0 ppm).

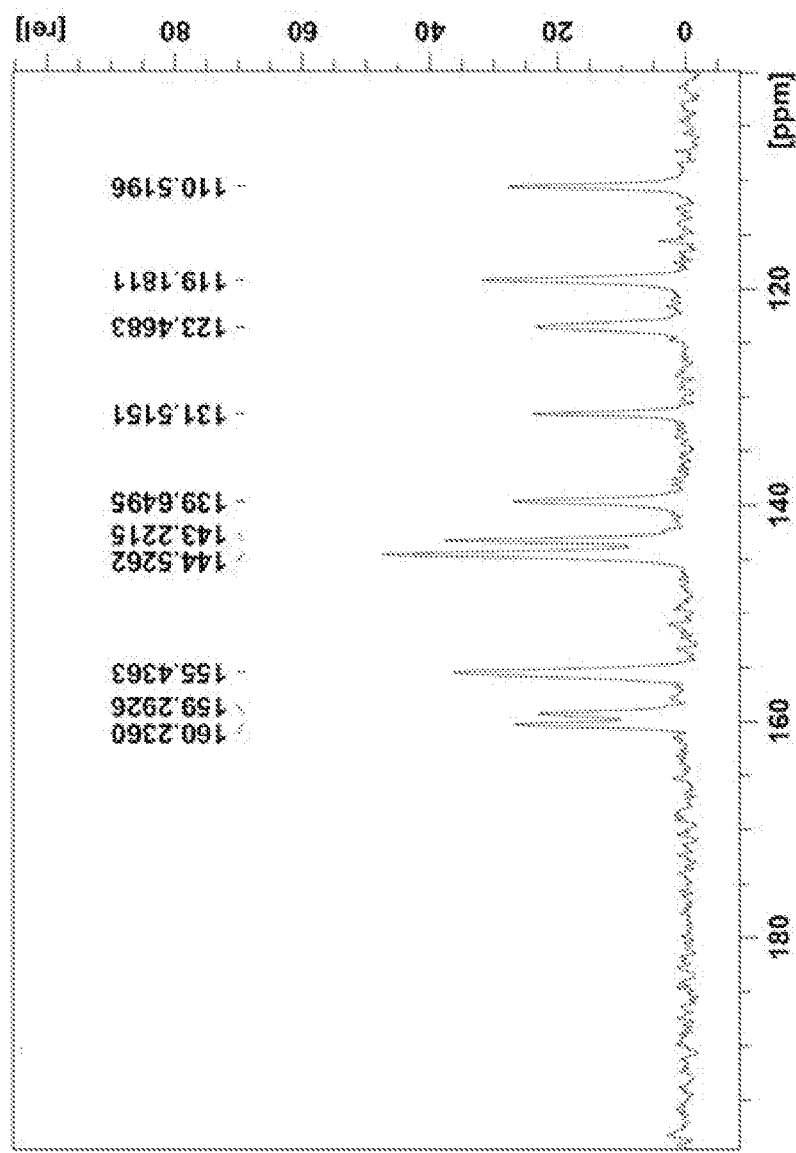
Figure 8. Solid State $^{13}$C NMR spectrum of Form E of Palbociclib dimesylate (zoomed- 200-100 ppm).

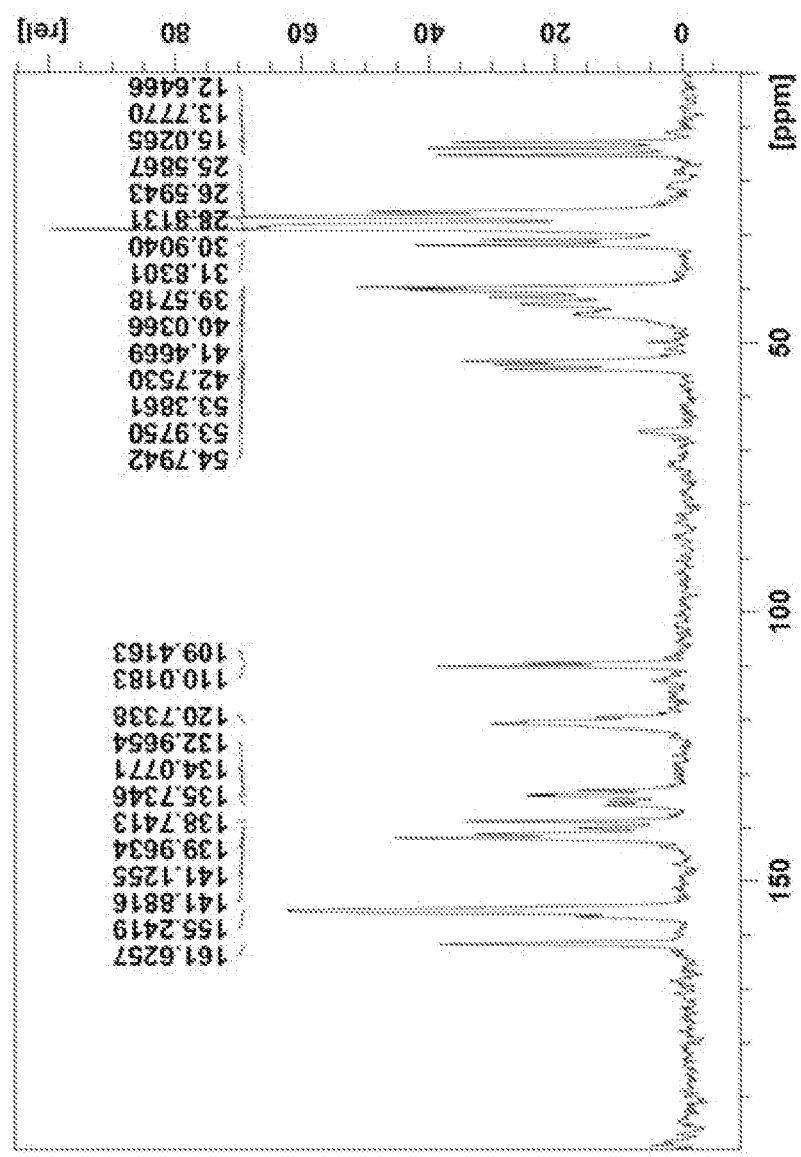
Figure 9. Solid State $^{13}$C NMR spectrum of Form F of Palbociclib dimesylate (Full range- 200-0 ppm).

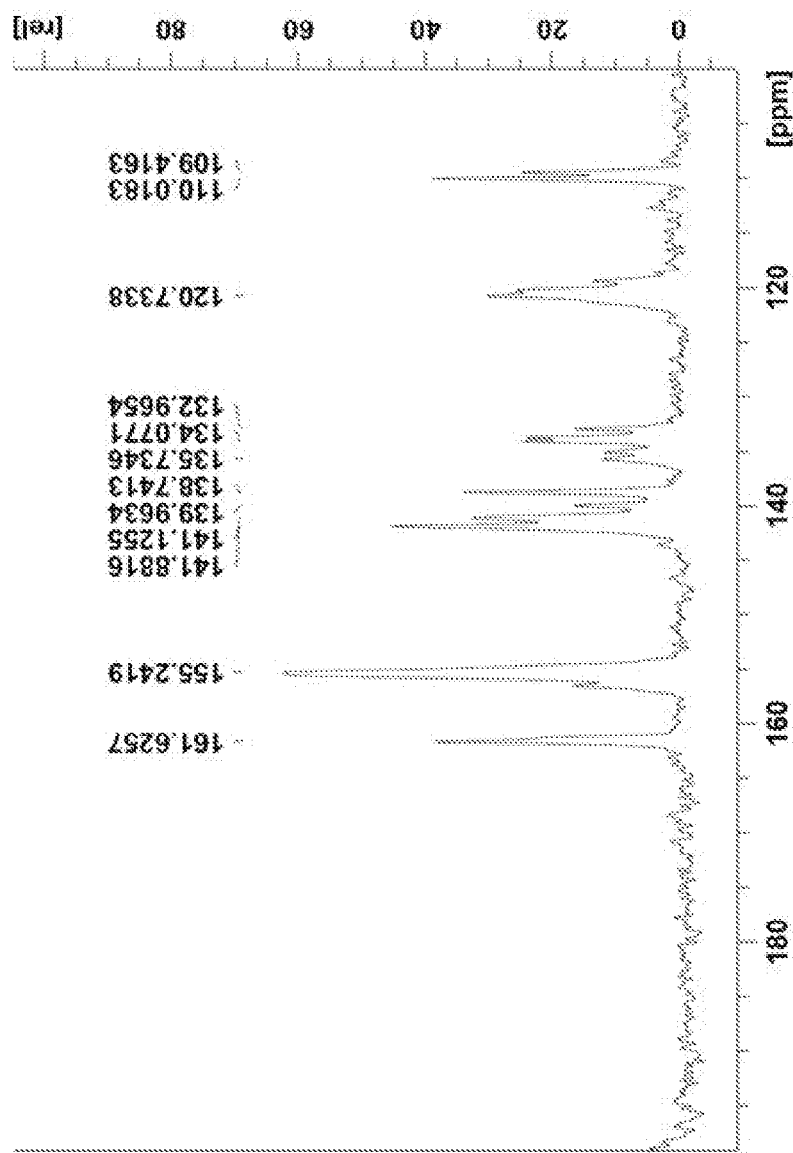
Figure 10. Solid State $^{13}$C NMR spectrum of Form F of Palbociclib dimesylate (zoomed- 200-100 ppm).

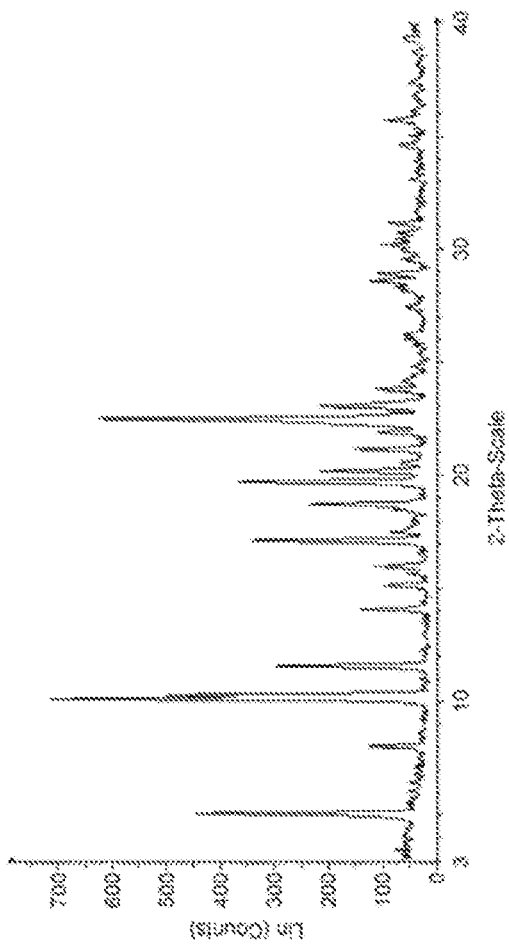
Figure 11. X-ray powder diffractogram of form A of Palbociclib from WO 2014/128588

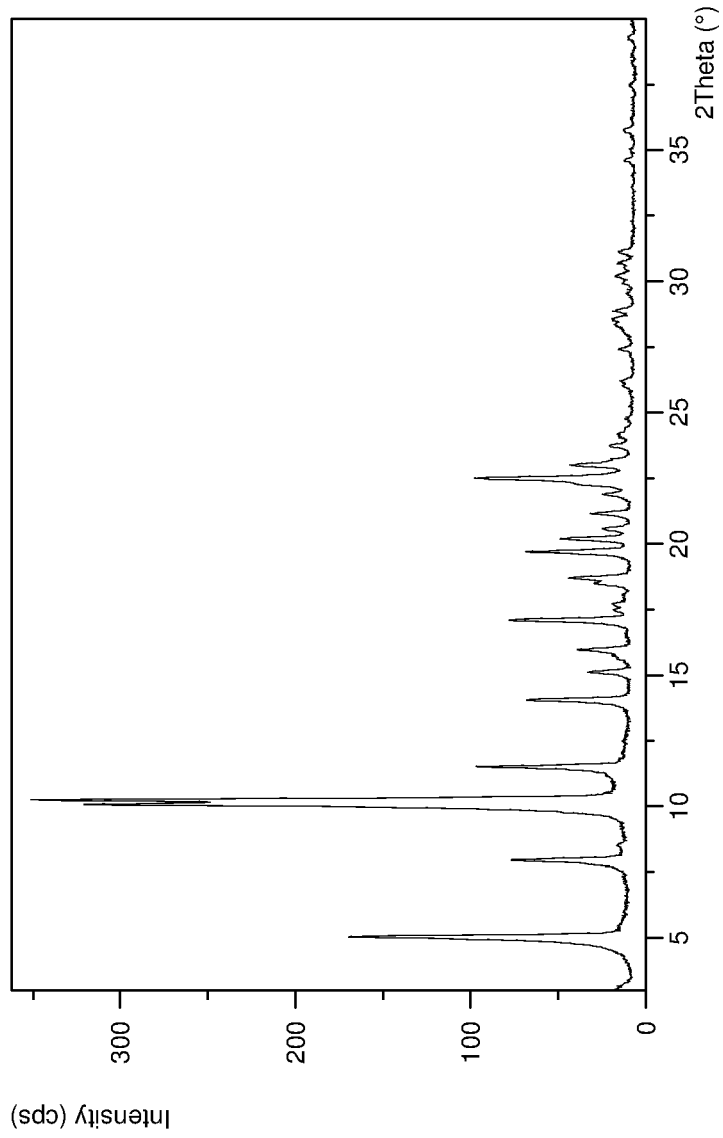
Figure 12. X-ray powder diffractogram of form A of Palbociclib obtained by example 6.

SOLID STATE FORMS OF PALBOCICLIB DIMESYLATE

CROSS-REFERENCE TO RELATED APPLICATIONS

This application is a continuation of U.S. application Ser. No. 16/315,816, filed Jan. 7, 2019, which is a National Stage application of PCT/US2017/041005, filed Jul. 7, 2017, which claims priority to United States Provisional Application No. 62/359,423, filed Jul. 7, 2016, the entire disclosures of each of which are incorporated herein by reference.

FIELD OF THE DISCLOSURE

The present disclosure encompasses solid state forms of Palbociclib dimesylate, processes for preparation thereof and use thereof for preparation of Palbociclib.

BACKGROUND OF THE DISCLOSURE

Palbociclib, 6-Acetyl-8-cyclopentyl-5-methyl-2-[[5-(1-piperazinyl)-2-pyridinyl]amino]pyrido[2,3-d]pyrimidin-7(8H)-one, has the following chemical structure:

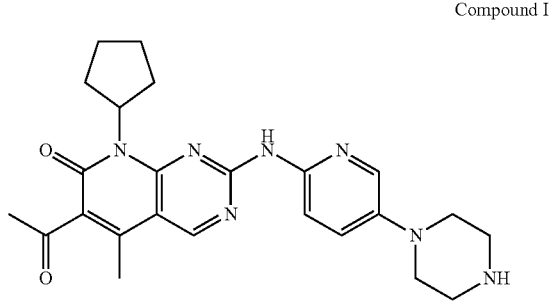 [SMILES: CC(=O)c1c(C)c2cnc(Nc3ccc(N4CCNCC4)cn3)nc2n(C2CCCC2)c1=O]

Compound I

Palbociclib is a kinase inhibitor indicated in combination with letrozole for the treatment of postmenopausal women with estrogen receptor (ER)-positive, human epidermal growth factor receptor 2 (HER2)-negative advanced breast cancer as initial endocrine-based therapy for their metastatic disease.

Palbociclib was described in WO 2003/062236. WO 2005/005426 described crystalline forms of isethionate, mesylate, dimesylate, HCl and di-HCl salts of Palbociclib. Further crystalline forms and amorphous form of Palbociclib HCl are described in WO 2016/066420. WO 2016/092442 and WO 2016/090257 describe crystalline forms of Palbociclib salts including phosphate, acetate, lactate, maleate, fumarate, citrate, succinate, L-tartarate, glutarate, adipate, glyconate, diesylate, hippurate, esylate and isethionate.

WO 2014/128588 discusses two crystalline forms, denominated A and B of Palbociclib.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Palbociclib.

Processes for preparation of Palbociclib were disclosed in WO 2003/062236, WO 2005/005426 and WO 2014/128588. The process development of Palbociclib is also discussed in Org. Process Res & Dev. 2016, 20, 1191-1202 (Duan et al.), 1203-1216 (Sutherland et al.) and 1217-1226 (Chekal et al).

However, Palbociclib obtained by prior art processes may typically contain the compound, 2-{[5-(1-piperazinyl)-2-pyridinyl]amino}-8-cyclopentyl-5-methylpyrido[2,3-d]pyrimidin-7(8H)-one, (herein designated as "Impurity A") as an impurity which is represented by the following structural formula:

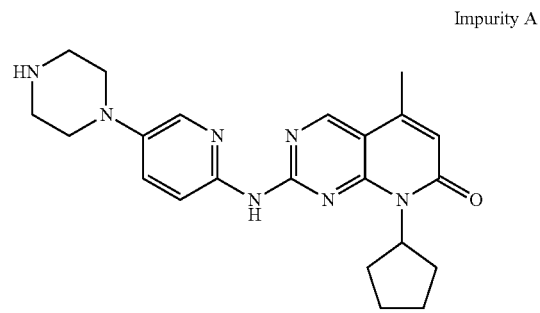 [SMILES: Cc1cc(=O)n(C2CCCC2)c2nc(Nc3ccc(N4CCNCC4)cn3)ncc12]

Impurity A

Impurity A is difficult to remove from the desired Palbociclib.

For at least these reasons, there is a need to develop robust processes for preparation of Palbociclib.

SUMMARY OF THE DISCLOSURE

The present disclosure provides solid state forms of Palbociclib dimesylate, processes for preparation thereof and use thereof for preparation of Palbociclib, solid state forms thereof, salts thereof and their solid state forms.

The present disclosure further provides solid state forms of palbociclib dimesylate for use in the preparation of Palbociclib, solid state forms thereof, salts thereof and their solid state forms.

The present disclosure further provides pharmaceutical compositions comprising Palbociclib dimesylate and pharmaceutical compositions comprising Palbociclib prepared by the processes of the present disclosure.

The present disclosure provides solid state forms of Palbociclib dimesylate for use in the preparation of pharmaceutical compositions of Palbociclib and salts thereof.

The present disclosure also encompasses the use of the Palbociclib dimesylate solid state forms of the present disclosure for the preparation of pharmaceutical compositions of Palbociclib and salts thereof.

The present disclosure comprises processes for preparing pharmaceutical compositions comprising Palbociclib dimesylate. The processes comprise combining Palbociclib dimesylate solid state forms or with at least one pharmaceutically acceptable excipient.

The present disclosure comprises processes for preparing pharmaceutical compositions comprising Palbociclib. The processes comprise combining Palbociclib prepared by the processes of the present invention with at least one pharmaceutically acceptable excipient.

The solid state forms and the pharmaceutical compositions of Palbociclib dimesylate of the present disclosure can be used as medicaments, particularly for the treatment of postmenopausal women with estrogen receptor (ER)-positive, human epidermal growth factor receptor 2 (HER2)-negative advanced breast cancer as initial endocrine-based therapy for their metastatic disease.

The present disclosure also provides methods of treating postmenopausal women with estrogen receptor (ER)-positive, human epidermal growth factor receptor 2 (HER2)-negative advanced breast cancer as initial endocrine-based therapy for their metastatic disease, comprising administering a therapeutically effective amount of a Palbociclib dimesylate solid state form of the present disclosure, or at least one of the above pharmaceutical compositions, to a subject in need of the treatment.

Palbociclib prepared by the processes of the present disclosure can be used as medicament, particularly for the treatment of postmenopausal women with estrogen receptor (ER)-positive, human epidermal growth factor receptor 2 (HER2)-negative advanced breast cancer as initial endocrine-based therapy for their metastatic disease.

The present disclosure also provides methods of treating postmenopausal women with estrogen receptor (ER)-positive, human epidermal growth factor receptor 2 (HER2)-negative advanced breast cancer as initial endocrine-based therapy for their metastatic disease, comprising administering a therapeutically effective amount of a Palbociclib prepared by the process of the present disclosure, or at least one of the above pharmaceutical compositions, to a subject in need of the treatment.

The present invention also provides the use of the solid state form of Palbociclib dimesylate of the present invention, or at least one of the above pharmaceutical compositions or formulations for the manufacture of a medicament for treating postmenopausal women with estrogen receptor (ER)-positive, human epidermal growth factor receptor 2 (HER2)-negative advanced breast cancer as initial endocrine-based therapy.

BRIEF DESCRIPTION OF THE DRAWINGS

FIG. 1 shows an X-ray powder diffractogram ("XRPD") of Form E of Palbociclib dimesylate.

FIG. 2 shows a potentiometric titration curve of Form E of Palbociclib dimesylate.

FIG. 3 shows an X-ray powder diffractogram ("XRPD") of Form F of Palbociclib dimesylate.

FIG. 4 shows an X-ray powder diffractogram ("XRPD") of a Form G of Palbociclib dimesylate.

FIG. 5 shows an FTIR spectrum of Form E of Palbociclib dimesylate.

FIG. 6 shows an FTIR spectrum of Form F of Palbociclib dimesylate.

FIG. 7 shows a solid state $^{13}$C NMR spectrum of Form E of Palbociclib dimesylate (Full range—200-0 ppm).

FIG. 8 shows a solid state $^{13}$C NMR spectrum of Form E of Palbociclib dimesylate (zoomed—200-100 ppm).

FIG. 9 shows a solid state $^{13}$C NMR spectrum of Form F of Palbociclib dimesylate (Full range—200-0 ppm).

FIG. 10 shows a solid state $^{13}$C NMR spectrum of Form F of Palbociclib dimesylate (zoomed—200-100 ppm).

FIG. 11 shows an X-ray powder diffractogram of form A of Palbociclib from WO 2014/128588.

FIG. 12 shows an X-ray powder diffractogram of form A of Palbociclib obtained by example 6.

DETAILED DESCRIPTION OF THE DISCLOSURE

The present disclosure provides solid state forms of Palbociclib dimesylate, processes for preparation thereof and use thereof for preparation of Palbociclib, solid state forms thereof, salts thereof and their solid state forms. Solid state properties of Palbociclib dimesylate can be influenced by controlling the conditions under which the Palbociclib dimesylate is obtained in solid form.

The products obtained by prior art processes may typically contain quantities of the compound, 2-{[5-(1-piperazinyl)-2-pyridinyl]amino}-8-cyclopentyl-5-methylpyrido[2,3-d]pyrimidin-7(8H)-one, (herein designated as "Impurity A") as an impurity which is represented by the following structural formula:

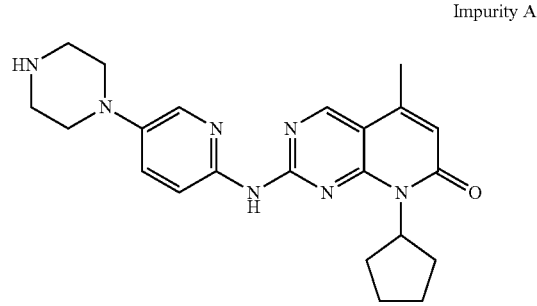 [SMILES: Cc1cc(=O)n(C2CCCC2)c2nc(Nc3ccc(N4CCNCC4)cn3)ncc12]

Impurity A

The routes for preparation of Palbociclib described in the literature are summarized in scheme I.

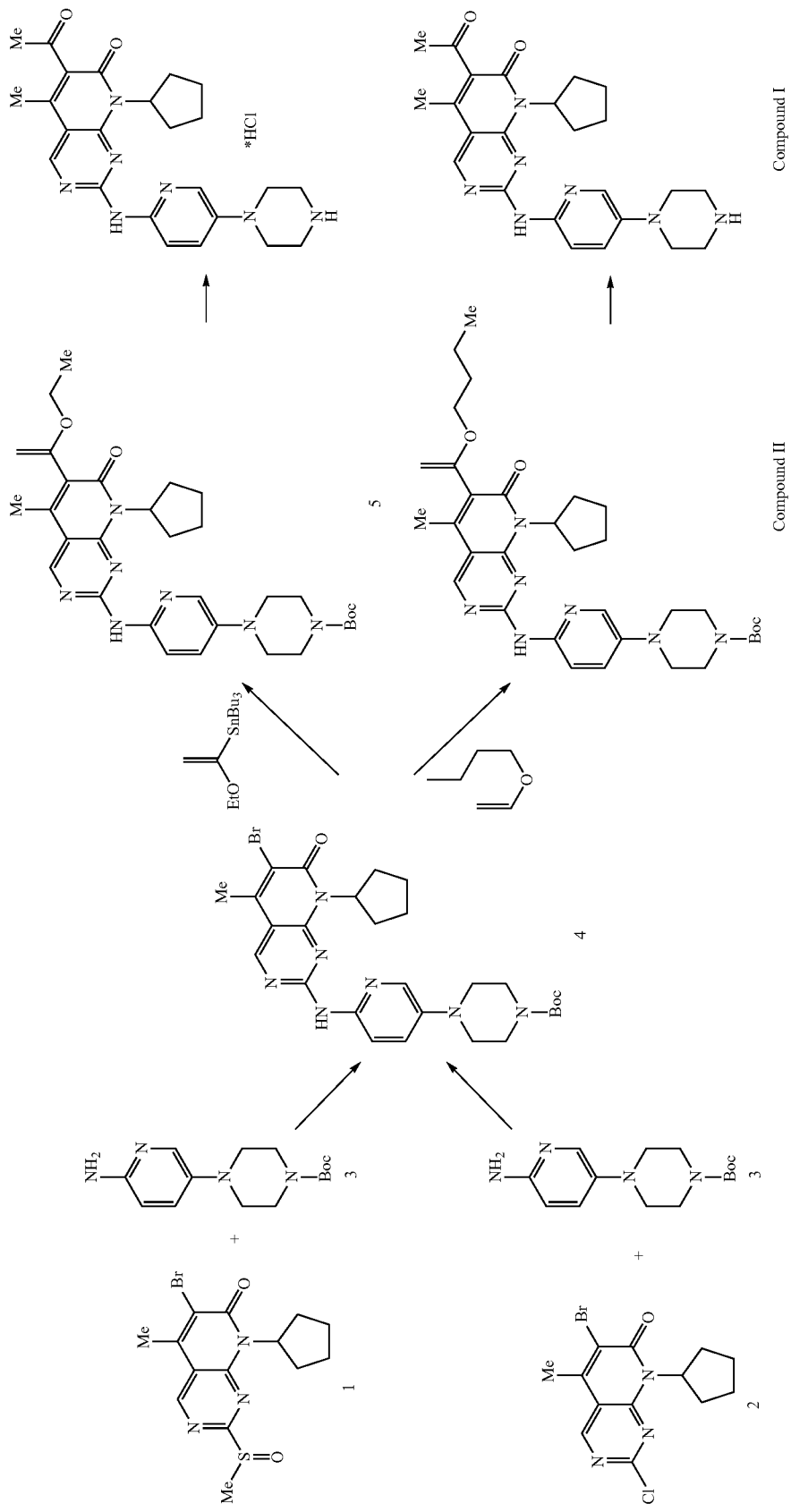
Scheme 1

Impurity A is apparently formed due to the presence of impurity A1 (represented by the following formula) in tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (designated herein compound II)

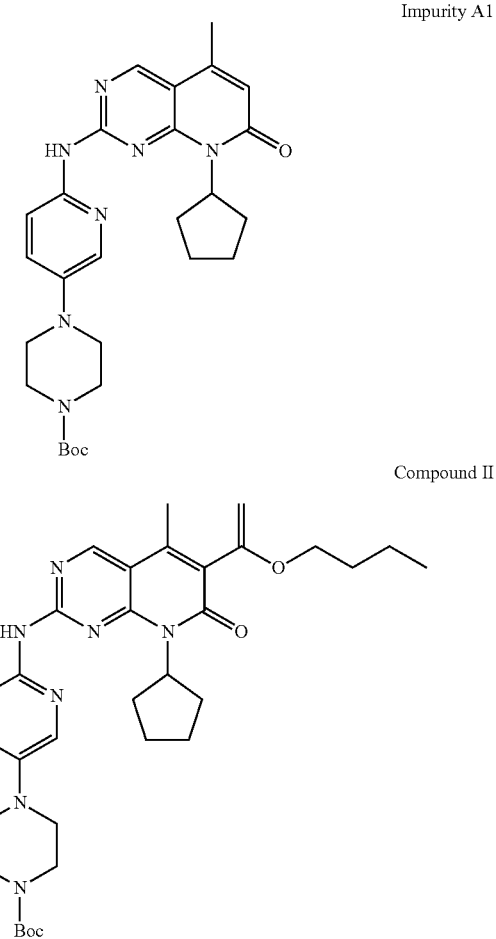

Impurity A1

Compound II

IPCOM000244149 discloses preparation of compound 4 containing controlled levels of impurity A1, that in turn leads to the formation of impurity A. However, Impurity A1 is also formed in the process for formation of the enol ether side chain by Heck coupling, i.e. in the formation of compound II.

Impurity A is difficult to remove from the desired product.

Conversion of compound II to palbociclib occurs in aqueous solvent mixtures using strong acids. It was surprisingly found that using methanesulfonic acid for this conversion leads to the formation of crystalline forms of palbociclib dimesylate, that offer significant impurity purging capability in that level of Impurity A or a salt thereof (particularly Impurity A mesylate or Impurity A dimesylate) in the solid state forms of palbociclib dimesylate of the present disclosure were lower than the levels of Impurity A1 in the compound of formula II before reaction and crystallization.

Further, the process of the present disclosure provides Palbociclib and/or Palbociclib dimesylate in overall high yield, and high quality, i.e. high chemical purity. Specifically, the process of the present disclosure provides Palbociclib which contains about 0.1% or less, preferably about 0.08% or less, more preferably 0.05% or less of 2-{[5-(1-piperazinyl)-2-pyridinyl]amino}-8-cyclopentyl-5-methylpyrido[2,3-d]pyrimidin-7(8H)-one herein designated as "impurity A") as an impurity. Therefore, the processes of the present disclosure can be adapted to production in an industrial scale, i.e., greater than 1 kilogram scale.

A solid state form (or polymorph) may be referred to herein as polymorphically pure or as substantially free of any other solid state (or polymorphic) forms. As used herein in this context, the expression "substantially free of any other forms" will be understood to mean that the solid state form contains 20% or less, 10% or less, 5% or less, 2% or less, or 1% or less of any other forms of the subject compound as measured, for example, by PXRD. Thus, solid state of Palbociclib dimesylate described herein as substantially free of any other solid state forms would be understood to contain greater than 80% (w/w), greater than 90% (w/w), greater than 95% (w/w), greater than 98% (w/w), or greater than 99% (w/w) of the subject solid state form of Palbociclib dimesylate. Accordingly, in some embodiments of the invention, the described solid state forms of Palbociclib dimesylate may contain from 1% to 20% (w/w), from 5% to 20% (w/w), or from 5% to 10% (w/w) of one or more other solid state forms of the same Palbociclib dimesylate.

Depending on which other solid state forms comparison is made, the crystalline forms of Palbociclib dimesylate of the present disclosure have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of palbociclib dimesylate referred to herein as being characterized by graphical data "as depicted in" or "as substantially depicted in" a Figure will thus be understood to include any crystal forms of Palbociclib dimesylate characterized with the graphical data having such small variations, as are well known to the skilled person, in comparison with the Figure.

As used herein, and unless stated otherwise, the term "anhydrous" in relation to crystalline forms of Palbociclib dimesylate relates to a crystalline form of Palbociclib dimesylate which does not include any crystalline water (or other solvents) in a defined, stoichiometric amount within the crystal. Moreover, an "anhydrous" form would typically not contain more than 1% (w/w) of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the term "isolated" in reference to solid state forms of Palbociclib dimesylate of the present disclosure corresponds to a solid state form of Palbociclib dimesylate that is physically separated from the reaction mixture in which it is formed.

As used herein, unless stated otherwise, PXRD peaks reported herein are preferably measured using CuK α radiation, λ=1.5418 Å. Preferably, PXRD peaks reported herein are measured using CuK α radiation, λ=1.5418 Å, at a temperature of 25±3° C. Alternatively, if an instrument with a different wavelength is used, for example, when using high resolution XRD method, such as synchrotron, the data may be corrected to wavelength of 1.5418 respectively.

As used herein crystalline form A of Palbociclib refers to a crystalline form as described in WO 2014/128588, which may be characterized by X-ray powder diffraction pattern as depicted in FIG. 11.

As used herein, unless stated otherwise, chemical purity (area percent) may be measured by HPLC analysis. Preferably, the HPLC analysis is carried out using a reversed phase column (e.g. C-18 column) using UV detection at 290 nm. Any suitable eluent can be used to carry out the separation (preferably acetonitrile is used). Chemical purity may also be measured by wt %.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 500 mbar.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

In one embodiment the present disclosure relates to a crystalline form of Palbociclib dimesylate designated form E. The crystalline form E of Palbociclib dimesylate can be characterized by data selected from one or more of the following: an XRPD pattern as depicted in FIG. 1; an XRPD pattern having peaks at 9.2, 10.0, 16.4, 18.2 and 21.9 degrees two theta±0.2 degrees two theta; an FT-IR spectrum substantially as depicted in FIG. 5; an FT-IR spectrum having absorptions at 3385, 1697, 1607, 1529, 1332, 913, 857 and 768 $cm^{-1}$±4 $cm^{-1}$; a solid state $^{13}C$ NMR spectrum substantially as depicted in FIG. 7 or in FIG. 8; a solid state $^{13}C$ NMR spectrum having peaks at 144.5, 143.2, 131.5, 123.5 and 119.2 ppm±0.2 ppm; a solid state 13C NMR spectrum having the following chemical shift absolute differences between said characteristic peaks at 144.5, 143.2, 131.5, 123.5 and 119.2 ppm±0.2 ppm and a reference peak at 110.5 ppm±1 ppm of 34.0, 32.7, 21.0, 13.0 and 8.7 ppm±0.1 ppm; and combinations of these data.

Crystalline form E of Palbociclib dimesylate may be further characterized by an XRPD pattern having peaks as described above and also having any one, two, three, four or five additional peaks selected from the group consisting of 6.0, 10.9, 12.7, 15.0 and 15.6 degrees two theta±0.2 degrees 2-theta±0.2 degrees two theta.

Crystalline form E of Palbociclib dimesylate may be characterized by the data set forth in the following table.

TABLE 1

| X-ray powder diffraction peaks of Form E of Palbociclib dimesylate |
| --- |
| peak position (degrees two theta ±0.2 degrees two theta) |
| 0.0 |
| 6.0 |
| 9.2 |
| 10.0 |
| 10.9 |
| 12.7 |
| 15.0 |
| 15.6 |
| 16.4 |
| 17.5 |
| 17.8 |
| 18.2 |
| 18.4 |
| 19.3 |

TABLE 1-continued

X-ray powder diffraction peaks of
Form E of Palbociclib dimesylate peak position (degrees two
theta ±0.2 degrees two theta)

20.1
21.3
21.9
22.1
22.8
23.1
23.8
24.4
24.9
25.6
26.7
27.6
29.1
30.3
31.2
31.6
32.6
33.1
38.8

Crystalline form E of Palbociclib dimesylate may be characterized by FT-IR spectrum having absorptions at 3385, 2960, 1697, 1652, 1607, 1581, 1529, 1500, 1457, 1421, 1379, 1361, 1332, 1302, 1283, 1173, 1119, 1042, 993, 973, 936, 913, 893, 857, 846, 827, 802, 779, 768, 750, 730, 677, 644, 630, 610, 567, 548, 538, 526 and 460 cm$^{-1}$±4 cm$^{-1}$. Crystalline form E of Palbociclib dimesylate may be characterized by FT-IR spectrum having absorptions at 3385, 2960, 1697, 1652, 1607, 1581, 1529, 1500, 1457, 1421, 1379, 1361, 1332, 1302, 1283, 1173, 1119, 1042, 993, 973, 936, 913, 893, 857, 846, 827, 802, 779, 768, 750, 730, 677, 644, 630, 610, 567, 548, 538, 526 and 460 cm$^{-1}$±4 cm$^{-1}$.

Crystalline form E of Palbociclib dimesylate may be characterized by a solid state 13C NMR spectrum having peaks at 160.2, 159.3, 155.4, 144.5, 143.2, 139.6, 131.5, 123.5, 119.2, 110.5, 54.9, 50.2, 44.9, 40.1, 39.2, 30.2, 25.0 and 15.4 ppm±0.2 ppm.

Crystalline form E of Palbociclib dimesylate may be characterized by each of the above characteristics alone/or by all possible combinations, e.g. an XRPD pattern having peaks at 9.2, 10.0, 16.4, 18.2 and 21.9 degrees two theta±0.2 degrees two theta and an XRPD pattern as depicted in FIG. 1.

In one embodiment of the present disclosure, form E of Palbociclib dimesylate is isolated.

Crystalline form E of Palbociclib dimesylate may be polymorphically pure.

In another embodiment the present disclosure relates to a crystalline form of Palbociclib dimesylate designated form F. The crystalline form F of Palbociclib dimesylate can be characterized by data selected from one or more of the following: an XRPD pattern as depicted in FIG. 3; an XRPD pattern having peaks at 6.7, 7.4, 9.4, 11.0 and 18.8 degrees two theta±0.2 degrees two theta; an FT-IR spectrum substantially as depicted in FIG. 6; an FT-IR spectrum having absorptions at 1701, 1655, 1619, 1583, 1541, 1210, 1041 and 924 cm−1±4 cm$^{-1}$; a solid state $^{13}$C NMR spectrum substantially as depicted in FIG. 9 or in FIG. 10; a solid state $^{13}$C NMR spectrum having peaks at 161.6, 141.9, 141.1, 138.7 and 133.0 ppm±0.2 ppm; a solid state $^{13}$C NMR spectrum having the following chemical shift absolute differences between said characteristic peaks at 161.6, 141.9, 141.1, 138.7 and 133.0 ppm±0.2 ppm and a reference peak at 110.0 ppm±1 ppm of 51.6, 31.9, 31.1, 28.7 and 23.0 ppm±0.1 ppm; and combinations of these data.

Crystalline form F of Palbociclib dimesylate may be further characterized by an XRPD pattern having peaks as described above and also having any one, two, three, four or five additional peaks selected from the group consisting of 8.0, 8.7, 13.5, 16.7 and 17.8 degrees two theta±0.2 degrees 2-theta±0.2 degrees two theta.

Crystalline form F of Palbociclib dimesylate may be characterized by the data set forth in the following table.

TABLE 2

X-ray powder diffraction peaks of
Form F of Palbociclib dimesylate peak position (degrees two
theta ±0.2 degrees two theta)

3.4
6.7
7.4
8.0
8.7
9.4
10.1
11.0
13.5
15.0
16.7
17.8
18.3
18.8
20.0
21.4
23.9
26.5

Crystalline form F of Palbociclib dimesylate may be characterized by FT-IR spectrum having absorptions at 3426, 2955, 2865, 1701, 1655, 1619, 1583, 1541, 1512, 1460, 1381, 1355, 1318, 1286, 1275, 1210, 1167, 1117, 1041, 949, 924, 893, 848, 801, 777, 741, 719, 678, 641, 625, 612, 553, 524, 468 and 455 cm$^{-1}$±4 cm$^{-1}$.

Crystalline form F of Palbociclib dimesylate may be characterized by a solid state $^{13}$C NMR spectrum having peaks at 161.6, 155.2, 141.9, 141.1, 140.0, 138.7, 135.7, 134.1, 133.0, 120.7, 110.0, 109.4, 54.8, 54.0, 53.4, 42.8, 41.5, 40.0, 39.6, 31.8, 30.9, 28.8, 26.6, 25.6, 15.0, 13.8 and 12.6 ppm±0.2 ppm Crystalline form F of Palbociclib dimesylate may be characterized by each of the above characteristics alone/or by all possible combinations, e.g. an XRPD pattern having peaks at 6.7, 7.4, 9.4, 11.0 and 18.8 degrees two theta±0.2 degrees two theta and an XRPD pattern as depicted in FIG. 3.

In one embodiment of the present disclosure, form F of Palbociclib dimesylate is isolated.

Crystalline form F of Palbociclib dimesylate may be polymorphically pure.

In another embodiment the present disclosure relates to a form of Palbociclib dimesylate designated form G. The crystalline form G of Palbociclib dimesylate can be characterized by data selected from one or more of the following: an XRPD pattern as depicted in FIG. 4; an XRPD pattern having peaks at 6.3, 7.2, 8.6, 9.3, 14.6, 16.4, 17.7 and 18.8 degrees two theta±0.2 degrees two theta, and combinations of these data.

In one embodiment of the present disclosure, form G of Palbociclib dimesylate is isolated.

Form G of Palbociclib dimesylate may be polymorphically pure.

The present invention encompasses processes for preparing Palbociclib, Palbociclib salts and their solid state forms. The process comprises preparing the crystalline forms of palbociclib dimesylate of the present disclosure and converting to Palbociclib, palbociclib salts and their solid state forms.

The conversion can be done, for example, by a process comprising basifying the crystalline forms of Palbociclib dimesylate of the present disclosure to obtain Palbociclib and optionally reacting the obtained Palbociclib base with an appropriate acid, to obtain the corresponding salt. Alternatively, palbociclib salts may be prepared by salt switching, i.e., reacting the solid state forms of palbociclib dimesylate of the present disclosure with an acid having a pKa which is lower than the pKa of methanesulfonic acid, to obtain the corresponding salt.

It was surprisingly found that the solid state forms of palbociclib dimesylate of the present disclosure offer significant impurity purging capability in that level of Impurity A A, or a salt thereof (in particular Impurity A mesylate or Impurity A dimesylate) in the solid state forms of palbociclib dimesylate of the present disclosure were lower than the levels of Impurity A1 in the compound of formula II before reaction and crystallization.

In one embodiment the solid state forms of palbociclib dimesylate of the present invention may contain about 0.2% area percent or less, preferably 0.1% area percent or less, more preferably about 0.08% area percent or less, particularly 0.04% area percent or less of Impurity A or a salt thereof (in particular, Impurity A mesylate or Impurity A dimesylate), as measured by HPLC. The solid state forms of Palbociclib dimesylate produced by the process according to any aspect or embodiment of the present invention may alternatively contain: ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of Impurity A or a salt thereof (in particular, Impurity A mesylate or Impurity A dimesylate) discussed above.

In another embodiment the solid state forms of Palbociclib dimesylate of the present invention may have a total impurity content of: not more than 0.4% area percent, preferably not more than 0.3% area percent, more preferably not more than 0.2% area percent, and particularly not more than 0.1% area percent, as measured by HPLC. The solid state forms of Palbociclib dimesylate according to any aspect or embodiment of the present invention may alternatively contain: ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of total impurities.

Therefore the solid state forms of palbociclib dimesylate of the present disclosure may be used as intermediates in the preparation of Palbociclib, preferably containing about 0.2% area percent or less, preferably 0.1% area percent or less, more preferably about 0.08% area percent or less, particularly 0.04% area percent or less of Impurity A, as measured by HPLC. Alternatively, the solid state forms of palbociclib dimesylate of the present disclosure may be used as intermediates in the preparation of Palbociclib, preferably containing ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of Impurity A.

Further, the solid state forms of palbociclib dimesylate of the present disclosure may be used as intermediates in the preparation of Palbociclib, preferably containing about 0.4% area percent or less, preferably 0.3% area percent or less, more preferably about 0.2% area percent or less, particularly 0.1% area percent or less of total impurities, as measured by HPLC. Alternatively, the solid state forms of palbociclib dimesylate of the present disclosure may be used as intermediates in the preparation of Palbociclib, preferably containing ≤1 wt %, ≤0.8 wt %, ≤05 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of total impurities.

The present disclosure provides the solid state forms of Palbociclib dimesylate for use for the preparation of palbociclib, preferably with the above discussed purity characteristics.

Palbociclib produced by the process of the present disclosure may preferably contain about 0.2% area percent or less, preferably 0.1% area percent or less, more preferably about 0.08% area percent or less, particularly 0.04% area percent or less of Impurity A. Alternatively, Palbociclib produced by the process of the present disclosure preferably contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of Impurity A discussed above.

Palbociclib produced by the process of the present disclosure may preferably contain about 0.4% area percent or less, preferably 0.3% area percent or less, more preferably about 0.2% area percent or less, particularly 0.1% area percent or less of total impurities. Alternatively, Palbociclib produced by the process of the present disclosure may preferably contain ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) of total impurities.

In some embodiments, the solid state forms of Palbociclib dimesylate of the disclosure are substantially free of any other forms of Palbociclib dimesylate, or of specified polymorphic forms of Palbociclib dimesylate, respectively.

In another aspect the disclosure relates to processes for preparation of Palbociclib. The processes of the present invention can be illustrated by the following Scheme 2:

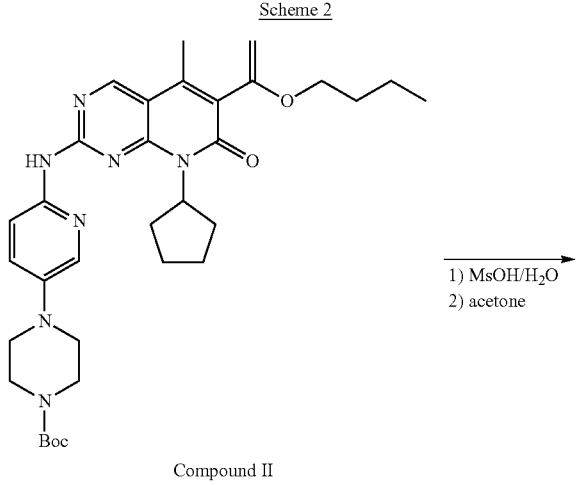

Compound II

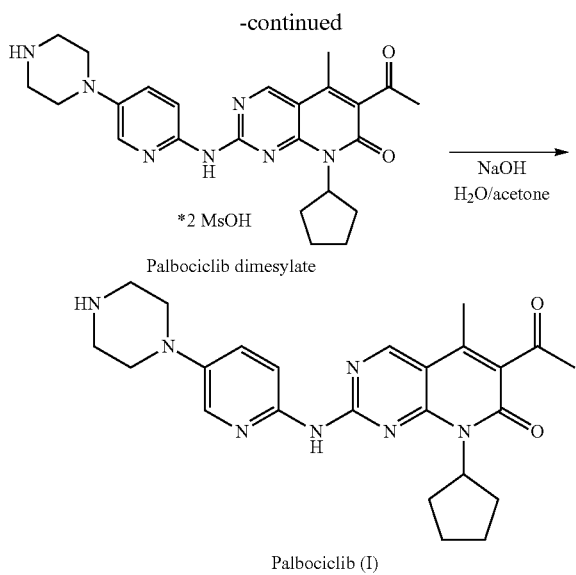

Palbociclib dimesylate

Palbociclib (I)

In another aspect the disclosure provides processes for preparing solid state forms of palbociclib dimesylate, preferably crystalline forms E, F and G of Palbociclib dimesylate, more preferably wherein the content of Impurity A or a salt thereof (in particular, Impurity A mesylate or Impurity A dimesylate) is 0.2% area percent or less, preferably 0.1% area percent or less, more preferably 0.08% area percent or less, particularly 0.04% area percent or less of Impurity A or a salt thereof (in particular, Impurity A mesylate or Impurity A dimesylate) discussed above comprising crystallizing palbociclib dimesylate from a mixture of water and acetone.

Alternatively, the disclosure provides processes for preparing solid state forms of palbociclib dimesylate, preferably crystalline forms E, F and G, more preferably wherein the content of total impurities is 0.4% area percent or less, preferably 0.3% area percent or less, more preferably 0.2% area percent or less, particularly 0.1% area percent or less comprising crystallizing palbociclib dimesylate from a mixture of water and acetone.

All of the discussed solid state forms of palbociclib dimesylate may be converted to palbociclib, solid state forms thereof, palbociclib salts and solid state forms of the salts.

In another aspect the disclosure relates to solid state forms of palbociclib dimesylate produced by the processes of the present disclosure.

In another aspect the disclosure relates to a process for preparation of Palbociclib, preferably wherein the content of Impurity A is 0.2% area percent or less preferably 0.1% area percent or less, more preferably 0.08% area percent or less, particularly 0.04% area percent or less of Impurity A, as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %), or wherein the palbociclib contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, which process comprises a) providing the solid state forms of Palbociclib dimesylate of the present disclosure; b) converting palbociclib dimesylate to palbociclib; c) separating the solid palbociclib formed; and d) optionally washing and/or drying Preferably step b of the process may comprise adding a base, preferably NaOH.

In another aspect the disclosure relates to a process for preparation of Palbociclib, preferably wherein the content of Impurity A is 0.2% area percent or less preferably 0.1% area percent or less, more preferably 0.08% area percent or less, particularly 0.04% area percent or less of Impurity A discussed above as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %), or wherein the palbociclib contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, which process comprises a) providing a solution of the state forms of Palbociclib dimesylate of the present disclosure in one or more solvents; b) converting palbociclib dimesylate to palbociclib; c) separating the solid palbociclib formed; and d) optionally washing and/or drying.

Preferably step a is performed in the presence of a polar protic solvent or a polar aprotic solvent or a mixture thereof, preferably water and acetone.

Preferably step b of the process comprises adding a suitable base. Suitable base may include inorganic and organic bases. Examples of suitable bases include but are not limited to NaOH, ammonia, sodium carbonate, amines, potassium carbonate, sodium bicarbonate. Preferably the base is NaOH.

In another aspect the disclosure provides a process for preparation of palbociclib preferably wherein the content of Impurity A is 0.2% area percent or less preferably 0.1% area percent or less, more preferably 0.08% area percent or less, particularly 0.04% area percent or less of Impurity A as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %), or wherein the palbociclib contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, comprising:

a) providing palbociclib dimesylate or solid state forms of palbociclib dimesylate of the present disclosure in a solvent system comprising a polar protic solvent or a polar aprotic solvent or a mixture thereof, preferably the solvent system comprises water and acetone and optionally stirring until dissolution;

b) adding a base, preferably NaOH, to adjust the pH to a value of from about 8 to about 14, preferably pH is adjusted to a value of about 12;

c) optionally separating the solid formed;

d) optionally washing and/or optionally drying to obtain palbociclib.

Preferably, in any of the processes described herein, the water to acetone ratio is from: about 1:1 to about 10:1, about 1:1 to about 5:1, about 1.2:1 to about 3:1 or about 1.4:1 to about 2:1, by volume.

In another aspect the disclosure relates to a process for preparation of Palbociclib, preferably wherein the content of Impurity A is 0.2% area percent or less, preferably 0.1% area percent or less, more preferably 0.08% area percent or less, particularly 0.04% area percent or less as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) or wherein the palbociclib contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, which process comprises:

a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) and methanesulfonic acid in a solvent system comprising one or more polar solvents, preferably the solvent system comprises water, and heating the reaction mixture to a temperature of from about 25° C. to about the reflux temperature of the solvent system; Alternatively, methanesulfonic acid may be added to compound II in the solvent system after heating the reaction mixture to a temperature of from about 25° C. to about the reflux temperature of the solvent system;

b) cooling the reaction mixture to a temperature lower than the temperature of step a but not less than about 0° C.;

c) optionally filtering;

d) adding a suitable anti solvent to afford a suspension;

e) cooling the suspension to a temperature of about 25° C. to about (−15)° C.;

f) filtering and optionally washing with the anti solvent used in step d to isolate palbociclib dimesylate; and g) converting palbociclib dimesylate to palbociclib.

Preferably the solvent system in step a) comprises water and the reaction mixture is heated to a temp of about 80° C. and in step b) the reaction mixture is cooled to a temp of about 50° C.

In a specific embodiment the solvent system in step a) consists essentially of water.

Suitable anti solvents for step d) of the above process, may include but are not limited to ketones, preferably a $C_3$-$C_8$ ketone, such as acetone, methyl ethyl ketone, diethyl ketone etc., ester solvents such as ethyl acetate, isopropyl acetate, butyl acetate etc. and alcohol solvents, preferably a $C_1$-$C_6$ alcohols, such as methanol, ethanol, propanol, isopropanol, etc.

Preferably the amount of anti-solvent added should afford a solvent mixture wherein the amount of the anti-solvent is at least about 4 volumes of anti solvent per one volume of solvent.

Preferably the anti solvent is ketone, preferably a C3-C8 ketone, or more preferably acetone.

In a particular embodiment the anti-solvent is acetone and the solvent mixture in step d consists essentially of acetone and water wherein at least about 4 volumes per one volume of water.

Preferably in step e the reaction mixture is cooled to about (−3)° C.

In another aspect the disclosure relates to a further process for preparation of Palbociclib, preferably wherein the content of Impurity A is 0.2% area percent or less, preferably 0.1% area percent or less, more preferably 0.08% area percent or less, particularly 0.04% area percent or less as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) or wherein the contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, which process comprises:

a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) and methanesulfonic acid in a solvent system comprising one or more polar solvents, preferably the solvent system comprises water, and heating the reaction mixture to a temperature of from about 25° C. to about the reflux temperature of the solvent system;

or providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in a solvent system comprising one or more polar solvents, preferably the solvent system comprises water, and heating the reaction mixture to a temperature of from about 25° C. to about the reflux temperature of the solvent and adding methanesulfonic acid;

b) optionally cooling the reaction mixture to a temperature lower than the temperature of step a but not less than about 0° C.;

c) optionally filtering;

d) adding a suitable anti solvent at a temperature of about 25° C. to about reflux temperature, preferably at a temp of about 50° C.;

e) optionally heating to reflux temperature;

f) cooling the reaction mixture to a temperature of about 25° C. to about (−15) ° C.;

g) separating the solid palbociclib dimesylate and optionally washing with the anti solvent used in step d); and h) converting palbociclib dimesylate to palbociclib.

Preferably the reaction mixture in step a) is heated to a temperature of about 80° C.

Steps b) and c) may be interchangeable, i.e. the optional cooling step may be performed before or after the optional filtering.

In a specific embodiment the solvent system in step a) consists essentially of water.

Suitable anti solvents for step d) of the above process, may include but are not limited to ketones, preferably a $C_3$-$C_8$ ketone, such as acetone, methyl ethyl ketone, diethyl ketone etc., ester solvents such as ethyl acetate, isopropyl acetate, butyl acetate etc. and alcohol solvents, preferably a $C_1$-$C_6$ alcohol, such as methanol, ethanol, propanol, isopropanol, etc.

Preferably the amount of anti solvent added is such to result in a solvent mixture wherein the ratio of anti-solvent to solvent is at least about 4:1 (v/v). Preferably the anti solvent is acetone In a particular embodiment the anti solvent is acetone and the solvent mixture in step d consists essentially of acetone and water preferably in a ratio of at least about 4 volumes per one volume of water.

Preferably in step f) the reaction mixture is cooled to about (−5) ° C.

In another aspect the disclosure relates to a process for preparation of Palbociclib, preferably wherein the content of Impurity A is 0.1% or less, 0.08% or less, more preferably 0.05% or less which process comprises:

a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in acetone and heating to a temperature of about 0° C. to about the reflux temperature, preferably to about 50° C.;

b) adding a solution of methanesulfonic acid in water;

c) keeping the suspension at a temperature of about 40° C. to about the reflux temperature preferably at about 50° C. to afford a cloudy solution;

d) cooling the reaction mixture to a temperature of about 0° C. to about 50° C., preferably to about 25° C.;

e) adding acetone and stirring;

f) filtering and optionally washing with the acetone to isolate palbociclib dimesylate; and g) converting palbociclib dimesylate to palbociclib.

Preferably the amount of acetone added in step d) should afford a solvent mixture wherein the amount of the acetone is at least about 4 volumes of per one volume of water.

In another aspect the disclosure relates to a further process for preparation of Palbociclib, preferably wherein the content of Impurity A is 0.2% area percent or less, preferably 0.1% area percent or less, more preferably 0.08% area percent or less, particularly 0.04% area percent or less as measured by HPLC or wherein the content of impurity A is ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt %) or wherein the palbociclib contains ≤1 wt %, ≤0.8 wt %, ≤0.5 wt %, ≤0.25 wt %, ≤0.2 wt %, ≤0.1 wt % or ≤0.05 wt % (preferably ≤0.2 wt %, ≤0.1 wt % or ≤0.05 wt %, and more preferably ≤0.1 wt % or ≤0.05 wt % of total impurities, which process comprises:

a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in a solvent system comprising water, and heating the reaction mixture to a temperature of about 80° C.;

b) adding methanesulfonic acid c) optionally cooling the reaction mixture to a temperature lower than the temperature of step a but not less than about 0° C., preferably to about 50° C.;

d) optionally filtering;

e) adding acetone at a temperature of about 25° C. to about reflux temperature, preferably at a temp of about 50° C.;

f) optionally heating to reflux temperature to get a solution;

g) cooling the reaction mixture to a temperature of about 25° C. to about (−15) ° C., more preferably about 0° C. to about (−10) ° C.;

h) separating the solid palbociclib dimesylate and optionally washing with acetone; and i) converting palbociclib dimesylate to palbociclib.

In a specific embodiment the solvent system in step a) consists essentially of water.

Steps c) and d) may be interchangeable, i.e. the optional cooling step may be performed before or after the optional filtering.

In a particular embodiment the solvent mixture in step e) consists essentially of acetone and water wherein the ratio of acetone to water is at least about 4 volumes of acetone per one volume of water.

Preferably in step g the reaction mixture is cooled to about (−5) ° C.

In a particular embodiment, the conversion of palbociclib dimesylate to palbociclib comprises the following steps:

A) providing palbociclib mesylate in a solvent system comprising a polar protic solvent or a polar aprotic solvent or a mixture thereof, preferably wherein the solvent system comprises water and acetone and optionally stirring until dissolution;

B) adding a base, preferably NaOH, to adjust the pH to about 8 to about 14, preferably about 12;

C) separating the solid palbociclib formed and optionally washing; and

D) optionally drying.

Preferably, in any of the processes described herein, the water to acetone ratio is from: about 1:1 to about 10:1, about 1:1 to about 5:1, about 1.2:1 to about 3:1 or about 1.4:1 to about 2:1, by volume.

The above solid state forms can be used to prepare other solid state forms of Palbociclib, palbociclib salts, and their solid state forms.

The present disclosure also provides solid state forms of Palbociclib dimesylate for use in the preparation of pharmaceutical compositions of Palbociclib and Palbociclib dimesylate.

The present disclosure further provides pharmaceutical compositions comprising Palbociclib dimesylate and pharmaceutical compositions comprising Palbociclib prepared by the processes of the present disclosure.

The present disclosure provides solid state forms of Palbociclib dimesylate for use in the preparation of pharmaceutical compositions of Palbociclib and salts thereof.

The present disclosure also encompasses the use of the Palbociclib dimesylate solid state forms of the present disclosure for the preparation of pharmaceutical compositions of Palbociclib and salts thereof.

The present disclosure comprises processes for preparing pharmaceutical compositions comprising Palbociclib dimesylate. The processes comprise combining Palbociclib dimesylate solid state forms or with at least one pharmaceutically acceptable excipient.

The present disclosure comprises processes for preparing pharmaceutical compositions comprising Palbociclib. The processes comprise combining Palbociclib prepared by the processes of the present invention with at least one pharmaceutically acceptable excipient.

The solid state forms and the pharmaceutical compositions of Palbociclib dimesylate of the present disclosure can be used as medicaments, particularly for the treatment of postmenopausal women with estrogen receptor (ER)-positive, human epidermal growth factor receptor 2 (HER2)-negative advanced breast cancer as initial endocrine-based therapy for their metastatic disease.

The present disclosure also provides methods of treating postmenopausal women with estrogen receptor (ER)-positive, human epidermal growth factor receptor 2 (HER2)-negative advanced breast cancer as initial endocrine-based therapy for their metastatic disease, comprising administering a therapeutically effective amount of a Palbociclib dimesylate solid state form of the present disclosure, or at least one of the above pharmaceutical compositions, to a subject in need of the treatment.

Palbociclib prepared by the processes of the present disclosure can be used as medicament, particularly for the treatment of postmenopausal women with estrogen receptor (ER)-positive, human epidermal growth factor receptor 2 (HER2)-negative advanced breast cancer as initial endocrine-based therapy for their metastatic disease.

The present disclosure also provides methods of treating postmenopausal women with estrogen receptor (ER)-positive, human epidermal growth factor receptor 2 (HER2)-negative advanced breast cancer as initial endocrine-based therapy for their metastatic disease, comprising administering a therapeutically effective amount of a Palbociclib prepared by the process of the present disclosure, or at least one of the above pharmaceutical compositions, to a subject in need of the treatment.

The present invention also provides the use of the solid state form of Palbociclib dimesylate of the present invention, or at least one of the above pharmaceutical compositions or formulations for the manufacture of a medicament for treating postmenopausal women with estrogen receptor (ER)-positive, human epidermal growth factor receptor 2 (HER2)-negative advanced breast cancer as initial endocrine-based therapy.

X-Ray Powder Diffraction ("XRPD") Method

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector.

Scanning parameters: angle range: 3-40 degrees 2-theta, step size 0.0167, time per step 37 s, continuous scan.

Measurement Parameters:

| | |
|---|---|
| Scan range | 3-40 degrees 2-theta |
| Scan mode | continuous |
| Step size | 0.0167 degrees |
| Time per step | 37 s |

Nuclear Magnetic Resonance (NMR) Method $^1$H (400 MHz) NMR spectra were recorded on Bruker Avance AV400 NMR spectrometer. D2O and DMSO were used as solvents. Chemical shifts (δ), in ppm, are referred to TMS as internal standard.

Potentiometric Titration Method

Potentiometric titration was performed on a Mettler Toledo DL 53 Instrument.

Materials:
Titrant: 0.1 N Sodium Hydroxide (NaOH)
Probe: DG111
Solvent: Water/Tetrahydrofuran 60:40 (v/v)

Sample Preparation and Procedure:

About 400 mg of accurately weighed palbociclib dimesylate were dissolved in 60 mL of Solvent and sonicated until complete dissolution.

Potentiometric titration was carried out using 0.1N NaOH and the volume added at the second point of inflexion was recorded.

Calculation:

$$\% \text{ Methanesulfonic Acid} = \frac{(V_{SA} - V_B) \times 0.1 \times F \times 96.10}{W} \times 100$$

VSA=mL of 0.1N NaOH used in Sample titration;
VB=mL of 0.1N NaOH used in Blank titration;
F=0.1N NaOH factor;
96.10=Methanesulfonic acid molecular weight;
W=Sample weight in mg.

HPLC Method Chromatographic Conditions
Column & packing: L-1, C-18, 150*4.6 mm*3.0 μm
Buffer: potassium phosphate monobasic about 15 mM, adjust pH 2.1±0.1 with 85% orthophosphoric acid solution
Eluent A: Buffer, Eluent B: ACN
Flow: 1.5 mL/min, Detector: 290 nm Gradient; Time: % Eluent B, (0-10, 16-40, 23-65, 30-65, 32-10)
Retention time peak of Palbociclib: about 6.7 min FT-IR Spectroscopy Method IR spectra were recorded on Nicolet 380 spectrometer equipped with KBr beam splitter and DTGS KBr detector, using ATR technique with ZnSe crystal.

Measurement Parameters:
Spectral range: 4000-400 cm$^{-1}$
Resolution: 4.0 cm$^{-1}$
Number of scans: 128
Sample gain: 8

$^{13}$C Solid-State NMR Method $^{13}$C CP/MAS NMR spectra were measured at 125 MHz using Bruker Avance III HD 500 WB/US NMR spectrometer (Karlsruhe, Germany, 2013) at magic angle spinning (MAS) frequency $\omega_r/2\pi$=11 kHz. In all cases finely powdered samples were placed into 4-mm ZrO2 rotors and the standard "cpmas" pulseprogram was used. During acquisition of the data the high-power dipolar decoupling SPINAL 64 was applied. The flip-pulse length was 4.8 μs. Applied nutation frequency of B1($^1$H) field was $\omega_1/2\pi$=89.3 kHz. Nutation frequency of B1($^{13}$C) and B1($^1$H) fields during cross-polarization was $\omega_1/2\pi$=62.5 kHz. The cross-polarization contact time was 2 ms. The $^{13}$C scale was calibrated with glycine as external standard (176.03 ppm—low-field carbonyl signal). Experimental details (key parameters such as repetition delay, D1, and number of scans, NS) for each of the measured samples are listed in Table 3.

The NMR spectrometer was completely calibrated and all experimental parameters were carefully optimized prior to the investigation of samples. Magic angle was set using KBr during standard optimization procedure and homogeneity of magnetic field was optimized using adamantane sample (resulting line-width at half-height $\Delta\nu_{1/2}$ was less than 3.5 Hz at 250 ms of acquisition time). Taking into account frictional heating of the samples during fast rotation all NMR experiments were performed at 305 K (precise temperature calibration was performed)

TABLE 3

Key parameters such as repetition delay, D1, and number of scans, NS) for each of the measured samples

| | D1, s | NS | T, K |
|---|---|---|---|
| Palbociclib dimesylate, Form E | 4 s | 500 | 305 K |
| Palbociclib dimesylate, Form F | 4 s | 808 | 305 K |

Specific Surface Area (SSA) Method

SSA measurement based on BET-nitrogen adsorption were carried out using a Micromeritics TriStar II Plus 3030 specific surface area analyzer together with Micromeritics VacPrep 061 degassing station.

Setup:
Software version: Microactive for TriStar II Plus v 2.03
Adsorbate: Nitrogen
Sample tube: ½" round bottom cell with glass filler rods
Sample masses*: Approximately % full cell
Sample preparation: VacPrep 061, nitrogen stream
Out gassing conditions: 16 hrs at 25° C. under vacuum
Isothermal jacket: Used
Isothermal collection points: 11 point BET in the range 0.05-0.30 P/Po Isothermal data analysis range: 7 point BET in the range 0.05-0.20 P/Po
Leak test: 120 s
Free space: Measured
Evacuation time: 1 hr
Outgas test duration: 180 s
Equilibration interval: 10 s
Equilibration timeout: 600 s
Calculations and Reporting: The specific surface area was reported in the range 0.05-0.20 P/Po using 7 point BET from a triplicate determination.

EXAMPLES

Example 1: Preparation of tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II)

tert-Butyl 4-(6-(6-(1-butoxyvinyl)-8-cyclopentyl-7,8-dihydro-5-methyl-7-oxopyrido[2,3-d]pyrimidin-2-ylamino) pyridin-3-yl)piperazine-1-carboxylate (5.6 kg) was suspended in n-butanol (28 L), n-butyl-vinyl ether (6.72 kg) and DIPEA (N,N-diisopropylethylamine) (2.18 L) were added, followed by a suspension of palladium acetate (43 g) and DPEPhos (bis[(2-diphenylphosphino)phenyl]ether), (206 g) in n-butanol (5.6 L). The mixture was heated at 80° C.

After reaction completion, water (0.84 L) was added and, after 45 min stirring at 80° C., the obtained solution was cooled and seeded (NB seeding step is optional). The suspension was cooled to 0° C. in 8 h and then stirred at 0° C. for 4 h. Upon filtration, washing with n-butanol (5.6 L) and drying at 60° C. under vacuum, the title compound was obtained (5.36 kg, 93% yield, 99.59% purity).

Example 2: Preparation of Palbociclib Dimesylate Form E

In a 500 ml reactor a mixture of water (34 ml, 2 v/w), acetone (51 ml, 3 v/w) and methanesulfonic acid (5.5 ml) was heated at 65° C. Compound II (17 g, purity—99.67 A %, Impurity A1 content—0.12 A %) was added portionwise in 90 min. The final suspension was cooled at 25° C., kept at this temperature for 16 h and then heated to reflux for 2 h, until complete dissolution of the solid material. Keeping the reflux, acetone (272 ml, 16 v/w) was added over 20 min: the final suspension was kept at reflux for 30 min and then cooled at 25° C. in 15 min and kept at this temperature for 16 h.

The suspension was filtered and washed with acetone. Upon drying in oven at 40° C. under vacuum, the title compound was obtained (17.2 g, yield 97.4%, purity 99.85 A %, Impurity A content—0.10 A %).

The product was analyzed by PXRD, indicating that Form E was obtained. The XRPD pattern is presented in FIG. 1.
Mesylate potentiometric titration: 29.9% (theoretical 30.0%)
NMR: DMSO; $^1H$, 400 MHz
2.43, 2.49, 2.52, 3.38, 3.54, 7.82, 8.16, 9.14 ppm Example 3: Preparation of Palbociclib Dimesylate Form F A. Procedure 1
In a 10 L reactor compound II (200 g, purity—99.59 A %, Impurity A1 content—0.09 A %) was loaded, followed by water (800 ml, 4 v/w) and methanesulfonic acid (95.5 g). The suspension was heated to 80° C. for 3 h, until a cloudy solution was obtained. The mixture was cooled to 50° C. and filtered, then acetone (4000 ml, 20 v/w) was added. The final suspension was cooled to −3° C. at 10° C./h rate.

The suspension was filtered and washed with acetone. Upon drying in oven at 40° C. under vacuum, the title compound was obtained (165 g, yield 77.9%, 99.9 A %, Impurity A content <0.04 A %).

The product was analyzed by PXRD, indicating that Form F was obtained. The XRPD pattern is presented in FIG. 3.
NMR: $D_2O$, $^1H$, 400 MHz
2.28, 2.39, 2.71, 3.39, 3.45, 7.37, 8.00, 8.90 ppm B. Procedure 2
In a 1000 ml reactor compound II (31 g, purity—99.12 A %, Impurity A1 content—0.26 A %) was suspended in acetone (93 ml, 3 v/w) and heated at 50° C. A solution of methanesulfonic acid (10 ml, 3 eq) in water (62 ml, 2 v/w on compound II) was added in 40 min. The suspension was kept at 50° C. for 16 h till dissolution, then cooled to 25° C. Acetone (550 ml, 17.7 v/w) was added over around 30 minutes keeping 25° C. and the final suspension was stirred at 25° C. for 1 h.

Upon filtration, washing with acetone and drying in oven at 40° C. under vacuum, the title compound was obtained (28.8 g, yield 105.3%, purity 99.62 A %, Impurity A content—0.15 A %). The product was analyzed by PXRD, indicating that Form F was obtained.

C. Procedure 3
In a reactor compound II (4.58 kg) was charged, followed by water (18.3 L). The mixture was stirred, while heating to 80° C. Once the target temperature was reached, methanesulfonic acid (2.19 kg) was slowly added, (over 120 minutes) in order to control foaming. At the end of the addition, the mixture was stirred at 80° C. for 1 h, then the resulting cloudy solution was filtered, washing lines and cartridge with water (2.5 L). Keeping the temperature around 50° C., acetone (109 L) was added (during 45 minutes). After addition, the reaction mixture was stirred for 5 minutes to afford a clear solution and then cooled to around 35° C. The resulting suspension was stirred for 2 hours, then cooled to −10±5° C. in about 5 h. Palbociclib Dimesylate suspension was stirred at −5° C. for 8 h, then filtered and washed with acetone. Upon drying in oven at 25-30° C. under vacuum, Palbociclib dimesylate was obtained as a yellowish solid (3.51 kg, 100% purity). The product was analyzed by PXRD, indicating that Form F was obtained.

Example 4: Preparation of Palbociclib Dimesylate Form G

In a 250 ml reactor, compound II (9 g) was suspended in water (86 ml 9.6 v/w) and acetone (42 ml, 4.7 v/w) at 25° C., methanesulfonic acid (7.16 g 5 eq) dissolved in a mixture of water (9 ml) and acetone (18 ml) was added and the mixture was heated at 50° C. for 5 h obtaining a cloudy solution.

After cooling at 25° C., the solution was filtered through a dicalite pad, then sodium hydroxide 10% water solution was added and the title compound precipitated off.

Upon filtration and washing with water and acetone, crude Palbociclib was dried under vacuum at 40° C. for 16 h (5.6 g, yield 86%)

In a 100 ml reactor, the crude palbociclib (5 g) was suspended in water (20 ml, 4 v/w) and methanesulfonic acid (20 ml, 4 v/w, 37 eq). The mixture was heated at 55° C. for 1 h obtaining a clear solution.

In a 500 ml reactor acetone (300 ml, 60 v/w) was prepared and, keeping the temperature at 25° C., the Palbociclib solution previously prepared was added in 5 min.

The obtained suspension was stirred for 5 min and then filtered.

Upon washing with acetone and drying in oven at 40° C. under vacuum, the title compound was obtained (5.5 g, yield 105%). The product was analyzed by PXRD, indicating that Form G was obtained. The XRPD pattern is presented in FIG. 4.

Example 5: Preparation of Palbociclib

Palbociclib dimesylate (30 g, obtained according to example 3, procedure 1) was suspended in water (468 ml) and acetone (292 ml) at 25° C., stirring until dissolution. Keeping the Palbociclib dimesylate solution at 25° C., a solution of sodium hydroxide 10% in water was added until pH=11, causing the precipitation of Palbociclib.

The suspension was stirred for 1 h, then filtered and washed with water and acetone. Upon drying in oven at 40° C. under vacuum, the title compound was obtained (18.3 g, yield 89%, purity 99.95%, Impurity A content <0.04%).

Example 6: Preparation of Palbociclib

Palbociclib dimesylate (3.51 kg) was suspended in water (40 L) and acetone (23 L). The suspension was stirred at 28° C. until dissolution. Aqueous sodium hydroxide (10% w/w) was added in 85 minutes, until pH=12, causing the precipitation of Palbociclib. The suspension was stirred for 20 minutes, then filtered and washed with water and acetone. Upon drying in oven at 45° C. under vacuum, the title compound was obtained (2.13 kg, yield 92%, purity 100.0%, SSA 4.9 m²/g). The product was analyzed by PXRD, indicating that Form A was obtained.

The invention claimed is:

1. A process for the preparation of Palbociclib comprising:
   (a) reacting tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) with methane sulfonic acid to form Palbociclib dimesylate, and
   (b) isolating the Palbociclib dimesylate; and
   (c) converting the Palbociclib dimesylate to Palbociclib, and wherein the Palbociclib contains about 0.4% area percent or less of total impurities, as measured by HPLC, or wherein the Palbociclib contains ≤1 wt% of total impurities.

2. A process according to claim 1 for the preparation of Palbociclib, which process comprises:
   a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) and methanesulfonic acid in a solvent system comprising one or more polar solvents, and heating the reaction mixture to a temperature of from about 25° C. to about the reflux temperature of the solvent system; or
   providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in a solvent system comprising one or more polar solvents, and heating the reaction mixture to a temperature of from about 25° C. to about the reflux temperature of the solvent and adding methanesulfonic acid;
   b) cooling the reaction mixture to a temperature lower than the temperature of step a) but not less than about 0° C.;
   c) optionally filtering;
   d) adding a suitable anti solvent to afford a suspension;
   e) cooling the suspension to a temperature of about 25° C. to about (−15)° C.;
   f) filtering and optionally washing with the anti solvent used in step d) to isolate palbociclib dimesylate; and
   g) converting the palbociclib dimesylate to palbociclib.

3. A process according to claim 1 for the preparation of Palbociclib, which process comprises:
   a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) and methanesulfonic acid in a solvent system comprising one or more polar solvents, and heating the reaction mixture to a temperature of from about 25° C. to about the reflux temperature of the solvent system; or
   providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in a solvent system comprising one or more polar solvents, and heating the reaction mixture to a temperature of from about 25° C. to about the reflux temperature of the solvent and adding methanesulfonic acid;
   b) optionally cooling the reaction mixture to a temperature lower than the temperature of step a) but not less than about 0° C.;
   c) optionally filtering;
   d) adding a suitable anti solvent at a temperature of about 25° C. to about reflux temperature;
   e) optionally heating to reflux temperature;
   f) cooling the reaction mixture to a temperature of about 25° C. to about (−15)° C.;
   g) separating solid palbociclib dimesylate and optionally washing with the anti solvent used in step d); and
   h) converting the palbociclib dimesylate to palbociclib.

4. A process according to claim 2, wherein step c) is performed prior to step b).

5. The process according to claim 3, wherein step d) is performed prior to step c).

6. A process according to claim 2 wherein the anti-solvent is a ketone.

7. A process according to claim 1, for the preparation of Palbociclib, which process comprises:
   a) providing tert-Butyl 4-[6-[[6-(1-Butoxyethenyl)-8-cyclopentyl-5-methyl-7-oxo-7,8-dihydro-pyrido[2,3-d]pyrimidin-2-yl]amino]-pyridin-3-yl]-piperazine-1-carboxylate (compound II) in a solvent system comprising water, and heating the reaction mixture to a temperature of about 80° C.;
   b) adding methanesulfonic acid;
   c) optionally cooling the reaction mixture to a temperature lower than the temperature of step a) but not less than about 0° C.;
   d) optionally filtering;
   e) adding acetone at a temperature of at least about 25° C. to about reflux temperature;
   f) optionally heating to reflux temperature to obtain a solution;

g) cooling the reaction mixture to a temperature of about 25° C. to about (−15)° C.;

h) separating solid palbociclib dimesylate and optionally washing with the acetone; and i) converting the palbociclib dimesylate to palbociclib.

8. The process according to claim 2 wherein the solvent system in step a) consists essentially of water.

9. The process according to claim 7 wherein the solvents in the reaction mixture in step e) consist essentially of acetone and water wherein the ratio of acetone to water is at least about 4 volumes of acetone per one volume of water.

10. The process according to claim 7 wherein in step g) the reaction mixture is cooled to a temperature of about (−5)° C.

11. The process according to claim 1 wherein the step of converting the palbociclib dimesylate to palbociclib comprises the following steps:

A) providing the palbociclib dimesylate in a solvent system comprising a polar protic solvent or a mixture thereof, and optionally stirring until dissolution;

B) adding a base, optionally in the form of aqueous solution, to adjust the pH to about 8 to about 14;

C) separating the solid palbociclib formed and optionally washing; and

D) optionally drying.

12. A process according to claim 1, wherein the Palbociclib contains: 0.2% area percent or less of Impurity A or a salt of Impurity A, as measured by HPLC or wherein the content of Impurity A is: ≤1 wt %.

13. A process according to claim 1, further comprising combining the Palbociclib with at least one pharmaceutically acceptable excipient to form a pharmaceutical composition.

* * * * *